(12) United States Patent
Klaubert et al.

(10) Patent No.: US 6,323,186 B1
(45) Date of Patent: Nov. 27, 2001

(54) PHOSPHATE-BOUND POLYAZAINDACENE DERIVATIVES OF NUCLEOTIDES

(75) Inventors: Dieter H. Klaubert, Sunnyvale, CA (US); Kyle R. Gee, Springfield, OR (US); Charles M. Brenner, Philadelphia, PA (US)

(73) Assignees: Molecular Probes, Inc., Eugene, OR (US); Thomas Jefferson University, Philadelphia, PA (US)

( * ) Notice: Subject to any disclaimer, the term of this patent is extended or adjusted under 35 U.S.C. 154(b) by 0 days.

(21) Appl. No.: 09/664,315

(22) Filed: Sep. 18, 2000

Related U.S. Application Data (60) Provisional application No. 60/154,485, filed on Sep. 17, 1999.

(51) Int. Cl.[7] .............................. A61K 31/70; C07H 21/04
(52) U.S. Cl. .............................. 514/47; 514/51; 536/24.3; 536/24.32; 435/6; 548/110; 424/9.1; 424/9.341
(58) Field of Search .............................. 536/24.3, 24.32; 435/6; 548/110; 514/47, 51; 424/9.1, 9.341

(56) References Cited

U.S. PATENT DOCUMENTS

| | | | |
|---|---|---|---|
| 4,774,339 | * | 9/1988 | Haugland et al. .................... 548/405 |
| 5,187,288 | | 2/1993 | Kang et al. . |
| 5,248,782 | | 9/1993 | Haugland et al. . |
| 5,274,113 | | 12/1993 | Kang et al. . |
| 5,338,854 | | 8/1994 | Kang et al. . |
| 5,728,529 | * | 3/1998 | Metzker et al. ......................... 435/6 |
| 5,928,884 | | 1/1999 | Croce et al. . |
| 6,005,113 | | 12/1999 | Wu et al. . |

OTHER PUBLICATIONS

Yarbrough et al., "Syntheis and properties of fluorescent nucleotide substrates for DNA–dependent RNA polymerases", J.Biol. Chem. 254(23)12069–12073 (1979).*
Pollack et al., "Fluorescent nucleotide triphosphate substrate for snake venom phosphodiesterase", Anal. Biochem. 127, 81–88 (1982).*
Schultz et al. J. Biol. Chem. 268, 6316 (1993).
Jencks, Catalysis in Chemistry and Enzymology (1987).
Pollack et al. Anal. Biochem. 127, 81–88 (1982).
Gasmi et al. Biochimica et Biophysica Acta 1405, 121–127 (1998).
Rotllán et al. FEBS Letters 429, 143–136 (1998).
Ji et al. Anal. Biochem. 271, 114–116 (1999).
Dhar et al. J. Biol. Chem. 274(21), 14568–14572 (1999).
Sato et al. Chem. Pharm. Bull 38(8), 2287–2289 (1990).
Ramos et al. Biochim. Biophys. Acta 1253, 103–111 (1995).
Sato et al. J. Chem. Res. (S) 390–391 (1994).
Bhattacharyya et al. J. Biol. Chem. 274(21) 14573–14578 (1999).
Yarbrough et al. J. Biol. Chem. 254(23) 12069–12073 (1979).

* cited by examiner

Primary Examiner—Ralph Gitomer
Assistant Examiner—Devesh Khare
(74) Attorney, Agent, or Firm—Allegra J. Helfenstein; Anton E. Skaugset (57) ABSTRACT

The invention relates to dipyrrometheneboron difluoride-substituted nucleotides substituted by a dipyrromethenboron difluoride label on a phosphate moiety. The nucleotides of the invention are useful in fluorescence assays, including protein binding assays and assays for hydrolase enzymes.

29 Claims, 1 Drawing Sheet

PHOSPHATE-BOUND POLYAZAINDACENE DERIVATIVES OF NUCLEOTIDES

This application claims the priority of provisional application Ser. No. 60/154,485, filed Sep. 17, 1999, which is hereby incorporated by reference.

This invention was made with Government support under grant no. CA75954 awarded by the National Cancer Institute (National Institutes of Health). The Government has certain rights in this invention.

FIELD OF THE INVENTION

The invention relates to dipyrrometheneboron difluoride-substituted nucleotides useful in protein binding assays and as fluorescent or fluorogenic substrates for enzyme-catalyzed cleavage.

BACKGROUND

A variety of dipyrrometheneboron difluoride dyes (4,4-difluoro-4-bora-3a,4a-diaza-s-indacenes) have previously been described (U.S. Pat. Nos. 4,774,339 to Haugland et al.; U.S. Pat. No. 5,274,113 to Kang et al.; U.S. Pat. No. 5,274,113 to Kang et al., U.S. Pat. No. 5,248,782 to Haugland et al.; U.S. Pat. No. 5,187,288 to Kang et al.; U.S. Pat. No. 5,338,854 to Kang et al.; U.S. Pat. No. 5,433,896 to Kang et al.; and application Ser. No. 08/856,422 by Wu et al., filed May. 14, 1997; all incorporated by reference). The above patents describe fluorescent dyes and conjugates of fluorescent dyes based on the dipyrrometheneboron difluoride core structure.

The present invention relates to dipyrrometheneboron difluoride derivatives of nucleotides. Nucleotides fill critically important roles in a variety of cellular processes, Binding and hydrolysis of nucleotides regulate transcription, translation, secretion, signal transduction, and cellular decisions that relate to programmed cell death and neoplastic transformation. The present invention describes dipyrrometheneboron difluoride-labeled nucleotides that are useful in the study the physiological effects of the free nucleotide in biological systems, including cells, cell extracts, cell homogenates, and purified, reconstituted or synthetic protein and enzyme systems.

In particular, the binding of nucleotides to selected proteins is readily investigated using the instant materials. For example, G proteins are a family of intracellular proteins that mediate plasma membrane, translocational, secretory and other types of signaling via nucleotide-binding. The GTP derivatives of the invention are bound by G proteins, and possess utility for studies of G protein binding, activity and inhibition by fluorescence methods.

Fhit is a member of the histidine triad superfamily of nucleotide-binding proteins. Fhit binds and cleaves dinucleoside polyphosphates, and has been identified as a tumor-suppressor that is often inactivated early in many common human cancers. The fluorescent or fluorogenic nucleotides of the invention possess utility for studies of binding, activity and inhibition of the Fhit enzyme and other enzymes. (U.S. Pat. No. 5,928,884 (1999), incorporated by reference).

While a variety of fluorescent dye conjugates of dipyrrometheneboron difluoride dyes have been described, the selection of fluorescent labels for enzyme substrates or in protein binding assays is typically problematic, as the electronic and spatial requirements of the binding site of the protein of interest are difficult to predict a priori. For example, it was determined that the S-terminus bound GTP-γ-S conjugate of OREGON GREEN dye (Molecular Probes, Inc.) was found to be stable with respect to hydrolysis by the Fhit enzyme.

While dipyrrometheneboron difluoride conjugates of nucleotides have been described previously, the fluorophore has been conjugated to either the base subunit, or the sugar subunit (some examples have been sold under the trademark CHROMATIDE fluorescent nucleotides by Molecular Probes, Inc.). Nucleotid,es labeled on the base have not been useful for analyzing protein interactions, and while nucleotides labeled on the sugar moiety are quickly bound by G-proteins, the nucleotide is then rapidly hydrolyzed and dissociates from the protein.

Nucleotide conjugates wherein the dipyrrometheneboron difluoride label is bound to the phosphate chain have not previously been described. The compounds of the invention have been found to possess utility for assays related to binding or enzymatic cleavage of nucleotides.

BRIEF DESCRIPTION OF THE DRAWINGS

FIG. 1: A plot of log remaining substrate fluorescence against time, as described in Example 8.

SUMMARY OF THE INVENTION AND DESCRIPTION OF THE PREFERRED EMBODIMENTS

In one aspect, the invention relates to dipyrrometheneboron difluoride-labeled nucleotides. In another aspect, the invention relates to the use of the labeled nucleotides to assay proteins.

The nucleotides of the invention comprise a fluorescent label bound to the phosphate of a nucleotide. The compounds of the invention have the general formula The nucleotide is optionally a monophosphate (k=1), a diphosphate (k=2) or a triphosphate (k=3). Each W is independently hydroxy, a salt of hydroxy, a biologically compatible ester of hydroxy, or an -X-LINK-FLUOR moiety, provided that exactly one W is an -X-LINK-FLUOR moiety.

In the -X-LINK-FLUOR moiety, X is O, S, or $NR^9$, where $R^9$ is H, or $C_1$–$C_6$ alkyl, LINK is a covalent linkage, and FLUOR is a borapolyaza-s-indacene dye.

The Y and Z moieties are independently hydroxy or hydrogen. Where both Y and Z are hydroxy, the sugar moiety is a ribose. Where Z is hydroxy and Y is hydrogen, or Z is hydrogen and Y is hydroxy, the sugar moiety is a deoxyribose. Where both X and Y are hydrogen, the sugar moiety is a dideoxyribose.

Where a W is a salt of hydroxy, the charge of the hydroxide is balanced by a biologically compatible positive counterion, as is well known in the art. Examples of positively charged counterions include, but are not limited to, alkali metal ions, alkaline earth metal ions, ammonium or substituted ammonium ions, and transition metal ions. In certain applications using the compounds of the invention, it is preferable that the counterions, when present, are $Ca^{2+}$, $Mg^{2+}$, or $Mn^{2+}$. Preferably, any necessary counterion is biologically compatible, that is, it is not toxic as used, and does not have a substantially deleterious effect on biomolecules.

Where a W is an ester of hydroxy, it is a biologically compatible ester, typically an alpha-acyloxyalkyl ester having 3–6 carbons. Alpha-acyloxyalkyl ester-derivatized nucleotides more freely penetrate cellular membranes, where intracellular esterases cleave the esters hydrolytically, producing the free phosphate within the cell. Preferably, the alpha-acyloxyalkyl ester is an acetoxymethyl ester ($CH_3CO_2CH_2$—) or pivaloyloxymethyl ester (($CH_3$)$_3CCO_2CH_2$—). Acetoxymethyl esters of phosphates have been prepared previously (Schultz et al. J. BIOL. CHEM. 268, 6316 (1993)).

BASE is a purine or pyrimidine base. Preferably, BASE is selected from adenine (A), guanine (G), hypoxanthine (H), xanthine (X), thymine (T), uracil (U), or cytosine (C). The BASE moiety is unsubstituted, or one of the aromatic carbon atoms of BASE is optionally substituted by $NH_2$, SH, Cl, Br, I, F or $N_3$. The structures of the preferred BASE moieties are shown below.

(A)

(G)

(H)

(X)

(T)

-continued

(U)

(C)

The nucleotides of the invention that incorporate an adenine or guanine base typically exhibit some quenching of the fluorescence of the fluorescent label. Such quenching may be enhanced by the substitution of halogen, preferably Br or I, on the base. Preferably the fluorescence of the FLUOR moiety is quenched greater than 50%, more preferably 75%, 80%, 85%, 90%, 95%, or 98% quenched. Nucleotides incorporating guanine bases exhibit quenching to a greater degree than nucleotides incorporating other bases.

In one aspect of the invention, the nucleotide is a triphosphate wherein the fluorophore is bound to the terminal phosphate, having the formula including the biologically compatible salts and esters of the above nucleotide, as described above.

Covalent Linkage

The LINK-X moiety is a covalent linkage that joins the nucleotide to the fluorescent label FLUOR.

The X moiety is selected from O, S, and $NR^9$, where $R^9$ is H, or $C_1$–$C_6$ alkyl. Preferably, the X moiety is S.

LINK is optionally a single covalent bond, or is a combination of stable chemical bonds, optionally including single, double, triple or aromatic carbon-carbon bonds, as well as carbon-nitrogen bonds, nitrogen-nitrogen bonds, carbon-oxygen bonds and carbon-sulfur bonds. LINK typically includes ether, thioether, carboxamide, sulfonamide, urea, urethane or hydrazine moieties. Preferred LINK moieties have 1–20 nonhydrogen atoms selected from the group consisting of C, N, O and S; and are composed of any combination of ether, thioether, amine, ester, carboxamide, sulfonamide, hydrazide bonds and aromatic or heteroaromatic bonds. Preferably LINK is a combination of single carbon-carbon bonds and carboxamide or thioether bonds. The longest linear segment of LINK preferably contains 4–10 nonhydrogen atoms including one or two heteroatoms. Examples of LINK include substituted or unsubstituted polymethylene, arylene, alkylarylene or arylenealkyl. In one embodiment, LINK contains 1–6 carbon atoms. In yet another embodiment, LINK has the formula —$(CH_2)_a$ (CONH(CH$_2$)$_b$)$_d$— (where the FLUOR moiety is bound at either terminus), where a is an integer from 0–5, b is an integer from 1–5 and d is 0 or 1.

Selected examples of functional groups useful for the preparation of the covalent linkages of the invention are shown in Table 1, where the covalent linkage results from the reaction of a selected electrophilic group with a nucleophilic group.

TABLE 1

Examples of some routes to useful covalent linkages

| Electrophilic Group | Nucleophilic Group | Resulting Covalent Linkage |
|---|---|---|
| activated esters* | amines/anilines | carboxamides |
| acrylamides | thiols | thioethers |
| acyl azides** | amines/anilines | carboxamides |
| acyl halides | amines/anilines | carboxamides |
| acyl halides | alcohols/phenols | esters |
| acyl nitriles | alcohols/phenols | esters |
| acyl nitriles | amines/anilines | carboxamides |
| aldehydes | amines/anilines | imines |
| aldehydes or ketones | hydrazines | hydrazones |
| aldehydes or ketones | hydroxylamines | oximes |
| alkyl halides | amines/anilines | alkyl amines |
| alkyl halides | carboxylic acids | esters |
| alkyl halides | thiols | thioethers |
| alkyl halides | alcohols/phenols | ethers |
| alkyl sulfonates | thiols | thioethers |
| alkyl sulfonates | carboxylic acids | esters |
| alkyl sulfonates | alcohols/phenols | ethers |
| anhydrides | alcohols/phenols | esters |
| anhydrides | aniines/anilines | carboxamides |
| aryl halides | thiols | thiophenols |
| aryl halides | amines | aryl amines |
| aziridines | thiols | thioethers |
| boronates | glycols | boronate esters |
| carboxylic acids | amines/anilines | carboxamides |
| carboxylic acids | alcohols | esters |
| carboxylic acids | hydrazines | hydrazides |
| carbodiimides | carboxylic acids | N-acylureas or anhydrides |
| diazoalkanes | carboxylic acids | esters |
| epoxides | thiols | thioethers |
| haloacetamides | thiols | thioethers |
| haloplatinate | amino | platinum complex |
| haloplatinate | heterocycle | platinum complex |
| halotriazines | amines/anilines | aminotriazines |
| halotriazines | alcohols/phenols | triazinyl ethers |
| imido esters | amines/anilines | amidines |
| isocyanates | amines/anilines | ureas |
| isocyanates | alcohols/phenols | urethanes |
| isothiocyanates | amines/anilines | thioureas |
| maleimides | thiols | thioethers |
| phosphoramidites | alcohols | phosphite esters |
| silyl halides | alcohols | silyl ethers |
| sulfonate esters | amines/anilines | alkyl amines |
| sulfonate esters | thiols | thioethers |
| sulfonate esters | carboxylic acids | esters |
| sullonate esters | alcohols | ethers |
| sulfonyl halides | amines/anilines | sulfonamides |
| sulfonyl halides | phenols/alcohols | sulfonate esters |

*Activated esters, as understood in the art, generally have the formula -COM, where M is a good leaving group (e.g. succinimidyloxy (-OC$_4$H$_4$O$_2$) sulfosuccinimidyloxy (-OC$_4$H$_3$O$_2$-SO$_3$H), -1-oxybenzotriazolyl (-OC$_6$H$_4$N$_3$); 4-sulfo-2,3,5,6-tetrafluorophenyl; or an aryloxy group or aryloxy substituted one or more times by electron withdrawing substituents such as nitro, fluoro, chloro, cyano, or trifluoromethyl, or combinations thereof, used to form activated aryl esters; or a carboxylic acid activated by a carbodiimide to form an anhydride or mixed anhydride -OCOR$^a$ or OCNR$^a$NHR$^b$, where R$^a$ and R$^b$, which may be the same or different, are C$_1$–C$_6$ alkyl, C$_1$–C$_6$ perfluoroalkyl, or C$_1$–C$_6$ alkoxy; or cyclohexyl, 3-dimethylaminopropyl, or N-morpholinoethyl).
**Acyl azides can also rearrange to isocyanates The Fluorophore

The FLUOR moiety is a polyazaindacene dye, typically having the formula

R$^7$ is N or C—R$^8$. Where R$^7$ is N, the dye is a triazaindacene. Where R$^7$ is C—R$^8$, the dye is a diazaindacene. Typically, R7 is C—R$^8$.

The substituents R$^1$, R$^2$, R$^3$, R4, R$^5$, R$^6$, and R$^8$, which may be the same or different, are hydrogen, halogen, nitro, sulfo, cyano, alkyl, perfluoroalkyl, alkoxy, alkenyl, alkynyl, cycloalkyl, arylalkyl, or acyl, wherein the alkyl portions of each contain fewer than 20 carbons, typically fewer than 10 carbons; or substituted or unsubstituted aryl or heteroaryl. Typically, no more than four of R$^1$–R$^8$, which may be the same or different, are non-hydrogen.

Alternatively, adjacent substituents R$_1$ and R$^2$, taken in combination, and R$^5$ and R$^6$, taken in combination, form fused 6-membered aromatic rings according to the formula where each fused ring is optionally and independently substituted, by hydrogen, halogen, nitro, sulfo, cyano, alkyl, perfluoroalkyl, alkoxy, alkenyl, alkynyl, cycloalkyl, alkylthio, alkylamido, amino, monoalkylamino, dialkylamino (wherein the alkyl portions of each contain fewer than 20 carbons, typically fewer than 10 carbons); or substituted or unsubstituted aryl, heteroaryl, aryl-amido, heteroaryl-amido, aryl-oxy, heteroaryl-oxy, aryl-amino, or heteroaryl-amino; or 1–2 additional fused benzo or heteroaromatic rings that are optionally unsubstituted or substituted.

The FLUOR moiety is attached to LINK at one of R$^1$–R$^6$ or R$^8$. Chemically reactive versions of polyazaindacene dyes useful for the preparation of the instant compounds are commercially available from MOLECULAR PROBES, INC. under the trademark BODIPY (Eugene, Oregon). Alternatively, the syntheses of polyazaindacene dyes and dye-conjugates has been detailed in previous patent publications, including U.S. Pat. No. 4,774,339 to Haugland et al.; U.S. Pat. No. 5,274,113 to Kang et al.; U.S. Pat. No. 5,274,113 to Kang et al.; U.S. Pat. No. 5,433,896 to Kang et al.; and Application Ser. No. 08/856,422 by Wu et al., filed May 14, 1997 (each incorporated by reference).

Selected preferred embodiments of the FLUOR moiety are listed below. In each case the dashed line indicates the point of attachment of the LINK moiety.

-continued

Method of Use

The nucleotides of the invention possess particular advantages in the analysis of a sample with respect to a particular protein or a class of proteins. The sample is optionally analyzed to detect the presence of a particular protein, or to assay the enzymatic activity of a particular protein. The analysis of the sample is optionally qualitative or quantitative.

In one aspect of the invention, the compounds of the invention are used to assay the binding of the nucleotide to a protein. This assay typically comprises adding to a sample of interest a compound of the invention, incubating the sample for a time sufficient for a protein present in the sample to bind to the compound (resulting in a detectable optical response), detection of the optical response, and correlation of the detectable optical response with binding of the compound to the protein by comparison with a standard. The assay is optionally used to discover, characterize and/or evaluate macromolecular or small molecules that compete with the nucleotides of the invention for binding with the proteins of interest.

In another aspect of the invention, the compounds of the invention are used to assay for enzymatic cleavage of the nucleotide. This assay typically comprises adding to a sample of interest a compound of the invention, incubating the sample for a time sufficient for an enzyme present in the sample to cleave the compound (resulting in generation of a hydrolysis product), detection of the hydrolysis product, and correlation of the generation of the hydrolysis product with the presence, activity, or location of the enzyme. The assay is optionally used to discover, characterize and/or evaluate macromolecular or small molecules that compete with the nucleotides of the invention for binding with the enzyme of interest, or that inhibit the activity of the enzyme of interest.

The labeled nucleotide of the invention can be cleaved by the enzyme of interest at a number of potential sites. Cleavage can occur between the base and the ribose moiety, or between the ribose moiety and the phosphate chain. Alternatively, where the nucleotide is a polyphosphate, cleavage can occur between the alpha- and beta-phosphate, between the beta- and gamma-phosphate, or between the fluorophore and the gamma-phosphate.

Sample Types

Typically, the sample comprises cells, cell extracts, cell homogenates, purified or reconstituted proteins, recombinant proteins, or synthesized proteins. Possible sources of cellular material used to prepare the sample of the invention include without limitation plants, animals, fungi, protists, bacteria, archae, or cell lines derived from such organisms. Animal cells or animal cell lines used to prepare the sample of the invention are normal or diseased, or are optionally utilized in the assay for the diagnosis of a disease such as cancer. In one embodiment of the invention, the cells of the sample are mammalian cells. Alternatively, the sample is essentially cell-free, and comprises purified proteins or cell extracts that bind and/or cleave the nucleotides, including enzymes and receptor proteins. In a preferred embodiment, the protein is a G protein and the nucleotide is a derivatized GTP. In another preferred embodiment, the protein is a hydrolase enzyme, more preferably a phosphodiesterase, most preferably the Fhit enzyme.

The sample typically further comprises buffering agents and salts selected to, and in an amount sufficient to, insure that the sample pH and ion composition is compatible with and appropriate for the protein or enzyme of interest.

Adding the Nucleotide to the Sample

The nucleotide is combined with the sample in a way that facilitates contact of the protein of interest and the nucleotide of the invention. By bringing the nucleotide and protein into contact is meant, for instance, mixing of a solution of the nucleotide with a sample that contains or is suspected of containing the protein of interest, or multiple proteins of interest. The protein used to practice the invention is optionally free in solution (including biological fluids or culture medium); enclosed within a biological structure (i.e. an organism or a discrete unit of an organism, including live or permeabilized cells); extracted from a biological structure (e.g. from lysed cells, tissues, organisms or organelles); or immobilized in or on a solid or semi-solid material or a membrane such as in an agar matrix or on a nylon membrane.

When used as probes for intracellular events, the nucleotide is generally introduced into a cell by pressure microinjection methods. Using a microscope (phase contrast) and micromanipulator, the target cell is pierced with a microinjection syringe and the nucleotide is introduced directly into the cytoplasm in a pressurized burst. The volume of injection must usually be less than about 10% of the total cell volume because cells can tolerate only a small increase in volume without disruption of the plasma membrane. The compounds of the invention are also suitable for use with a variety of cultured cells.

Alternative methods of introducing the nucleotide into the cytoplasm include scrape loading techniques (short mechanical disruption of the plasma membrane where the plasma membrane is peeled away from the cytoplasm, the nucleotide is perfused through the sample and the plasma membrane is reassembled), patch clamp methods (where an opening is maintained in the plasma membrane for long periods), the use of osmolarity regulating agents (used to create micropores or channels in cell membranes), or phagocytosis. Any other treatment that will permeabilize the plasma membrane, such as electroporation, shock treatments or high extracellular ATP can be used to introduce the nucleotide into the cellular cytoplasm.

Typically, where the nucleotide is poorly water soluble, it is first dissolved in a water miscible solvent such as dimethylsulfoxide (DMSO) to facilitate its dispersion in the biological sample. Where a nucleotide of the invention is used as a probe in a sample that contains isolated proteins or cell extracts, the probe is generally combined with the sample by simple dissolution, using an organic solvent if necessary to dissolve the probe.

Where the instant assay is probing for enzymatic cleavage, the nucleotide is combined with the sample under conditions suitable for substrate cleavage. While the resulting cleavage products are typically readily detectable, in some cases the presence or degree of cleavage may be more readily determined by separation of the cleavage products from the nucleotide of the invention. The cleavage products are optionally separated by chromatography, electrophoresis, precipitation, affinity methods, or any other method that results in physical separation of the fluorescent hydrolysis product from the substrate precursor. In one embodiment, thin layer chromatography results in sufficient separation of the cleavage products from the uncleaved nucleotide to permit analysis of the assay by standard fluorescence methods.

Illumination

Preferably, either binding of the labeled nucleotide of the invention to a protein, or cleavage of the FLUOR moiety from the remainder of the molecule results in a detectable optical response. A detectable optical response means a change in, or occurrence of, an optical signal that is detectable either by observation or instrumentally. Typically the detectable response is a change in fluorescence, such as a change in the intensity, excitation or emission wavelength distribution of fluorescence, fluorescence lifetime, fluorescence polarization, or a combination thereof. The degree, location, and/or quality of fluorescence emission, compared with a standard or expected response, indicates whether and to what degree the sample possesses a given characteristic. Examples of such sample characteristics include the presence or absence of a particular protein, the activity or inactivity of a particular enzyme, the presence or absence of a competitive binding agent, or the presence or absence of an enzyme inhibitor.

The optical response is optionally detected by visual inspection, or by use of any of the following devices: CCD cameras, video cameras, photographic film, laser-scanning devices, fluorometers, photodiodes, quantum counters, epifluorescence microscopes, scanning microscopes, flow cytometers, imaging cytometers, fluorescence microplate readers, or by means for amplifing the signal such as photomultiplier tubes. Where the sample is examined using a flow cytometer, examination of the sample optionally includes sorting components of the sample according to their fluorescence response.

Typically, where the assay of the invention is detection of the binding of the nucleotide to a protein, the detectable optical response is a change in fluorescence intensity, fluorescence lifetime, or fluorescence polarization. The binding of GTP nucleotides of the invention by G-proteins typically results in restoration of the fluorescence of the FLUOR moiety, permitting analysis of G-protein binding by fluorescence methods. Alternatively, competitive binding molecules that displace the nucleotides of the invention (and result in a decrease of fluorescence) may also be evaluated using fluorescence methods. It is understood that a variety of detectable optical responses may be used in combination with the methods of the invention, including fluorescence lifetime and fluorescence polarization.

Preferably, where the assay of the invention is detecting cleavage of the nucleotide of the invention, the detectable optical response is a change in fluorescence intensity. In one embodiment, the nucleotide of the invention exhibits quenched fluorescence with respect to the cleavage product (typically for derivatives of GTP). In another embodiment, the nucleotide of the invention exhibits enhanced fluorescence with respect to the cleavage product. Preferably, the cleavage products exhibit enhanced fluorescence relative to the nucleotide of the invention, more preferably at least 2-fold fluorescence enhancement, even more preferably at least 4-fold enhancement.

Additional Detection Reagents

When used in complex biological systems, such as in vitro biological model systems or biological cells, the assays of the instant invention are optionally combined with the use of one or more additional detection reagents, such as an antibody, or a stain for another component of the system such as a nucleic acid stain, an organelle stain, a metal ion indicator, a probe to assess viability of the cell, or fluorescent microspheres. The additional detection reagent is optionally a fluorescent reagent exhibiting a color that contrasts with the fluorophore present in the assay, or is a label that is detectable by other optical or non-optical properties.

Kits

One aspect of the instant invention is the formulation of kits that facilitate the practice of the methods of the invention, as described above. The kit of the invention comprises a nucleotide of the invention. Typically, the kit further comprises one or more buffered solutions. The kits of the invention optionally further comprise additional detection reagents, fluorescent standards, enzymes, enzyme inhibitors, or instructions for carrying out an assay of the invention. The kits of the invention optionally further include materials and/or instrumental accessories so as to facilitate high throughput screening methods, including microwell plates, or microfluidic chips.

In one embodiment, the kit is useful for the detection or quantitation of hydrolase enzymes, in particular phosphodiesterase enzymes, most particularly the Fhit enzyme. In another embodiment, the kit is useful for investigating binding of the nucleotide of the invention to proteins, in particular G-proteins.

The examples below are given so as to illustrate the practice of this invention. They are not intended to limit or define the entire scope of this invention.

EXAMPLES

Example 1

Preparation of Compounds 1 and 2

The following compounds are prepared:

Compound 1

Compound 2

The tetralithium salt of ATP-γ-S and GTP-γ-S, respectively (25 mg, Sigma 85% pure, 0.05 mmol) is dissolved in 3 mL water, buffered to pH 9.0 with sodium bicarbonate. Equimolar amounts of the thiol-reactive dye N-(4,4-difluoro-5,7-dimethyl-4-bora-3a,4a-diaza-s-indacene-3-yl)methyl)iodoacetamide is added in 3.0 mL dioxane. The reaction mixture is stirred and the progress of the reaction is monitored by silica gel TLC using dioxane:2-propanol:water:ammonium hydroxide (40:20:35:35) as the mobile phase. ATP-γ-S and GTP-γ-S and the unreacted dye migrate with Rf values of 0.25, 0.20 and 0.95, respectively, while the fluorescent ATP conjugate (Compound 1) has an $R_f$ of 0.7, and the GTP conjugate (Compound 2) has an Rf of 0.65.

After several hours, when the reaction is virtually complete by TLC, the reaction mixture is concentrated via rotary evaporation to a volume of 2 mL. The crude solution is applied to an aqueous 2×30 cm column of SEPHADEX LH-20. Pooling and lyophilization of pure product fractions affords the desired nucleotide-dye conjugates with a yield of 76%–86%.

Example 2

Preparation of Compound 3

The following compound is prepared:

To a solution of GTP-γ-S (16.5 mg, 0.03 mmol, tetralithium salt, Sigma) in 2 mL water is added a solution of BODIPY 493/503 methyl bromide reactive dye (10 mg, 0.03 mmol, Molecular Probes, Eugene, Oregon) in 3 mL dioxane. Saturated sodium bicarbonate solution (2 drops) is added and the resulting red mixture is stirred at room temperature overnight. The volatiles are removed in vacuo, and the resulting residue is purified by column chromatography on SEPHADEX LH-20 using water as eluant. The desired product migrates through the column more slowly than any residual GTP-γ-S, but more rapidly than any residual reactive dye (silica gel TLC Rfs are 0.15 for starting nucleotide, 0.78 for the title compound, and 0.95 for starting dye using dioxane:2-propanol:water:ammonium hydroxide (40:20:35:35) as eluant). Pure product fractions are pooled and lyophilized to give Compound 3 as 17 mg (68%) of a red-orange powder.

Example 3
Preparation of Compound 4
The following compound is prepared:

To a solution of GTP-γ-S (5 mg, 0.01 mmol, tetralithium salt, Sigma) in 1 mL water is added a solution of BODIPY TR cadaverine iodoacetamide reactive dye (5 mg, 0.01 mmol, Molecular Probes Eugene, Oreg.) in 1 mL dioxane. Saturated sodium bicarbonate solution (1 drop) is added and the resulting purple solution is stirred at room temperature overnight. The volatiles are removed in vacuo, and the residue is purified by column chromatography on SEPHADEX LH-20 using water as eluant. The desired product migrates through the column more slowly than any residual GTP-γ-S, but more rapidly than any residual reactive dye (silica gel TLC Rfs are 0.15 for starting nucleotide, 0.73 for the title compound, and 0.95 for starting dye using dioxane:2-propanol:water:ammonium hydroxide (40:20:35:35) as eluant). Pure product fractions are pooled and lyophilized to give Compound 4 as 6 mg (60%) of a purple powder.

Example 4
Preparation of Compound 5
The following compound is prepared:

To a solution of GDP-β-S (11 mg, 0.02 mmol, trilithium salt, Sigma) in 1.5 mL water is added a solution of BODIPY FL iodoacetamide reactive dye (10 mg, 0.02 mmol, Molecular Probes, Eugene, Oreg.) in 1.5 mL dioxane. Saturated sodium bicarbonate solution (2 drops) is added and the resulting orange solution is stirred at room temperature overnight. The volatiles are removed in vacuo, and the residue is purified by column chromatography on SEPHADEX LH-20 using water as eluant. The desired product migrates through the column more slowly than any residual GDP-β-S, but more rapidly than any residual reactive dye (silica gel TLC $R_f$s are 0.28 for starting nucleotide, 0.76 for the title compound, and 0.95 for starting dye using dioxane:2-propanol:water:ammonium hydroxide (40:20:35:35) as eluant). Pure product fractions are pooled and lyophilized to give 22 mg of the orange Compound 5 as the sodium salt.

Example 5
Preparation of Compound 6
The following compound is prepared:

To a 10 mM aqueous solution of 5'-GTP, sodium salt, is added 2 equivalents of 1-(3-dimethylaminopropyl)-3-ethylcarbodiimide hydrochloride. To the resulting solution is added a 10 mM solution of 1.0 equivalent of BODIPY FL ethylenediamine reactive dye (Molecular Probes, Eugene, Oreg.), which has been previously adjusted to pH 7.0 by addition of aqueous NaOH. The reaction solution is stirred at room temperature, and the pH is maintained at 6 by periodic addition of aqueous HCl. After several hours the reaction solution is purified by either column chromatography using water on SEPHADEX LH-20 or ion-exchange column chromatography on DEAE-cellulose using 0.05–0.5 M ammonium bicarbonate as eluant. In either case unreacted nucleotide elutes first, followed by Compound 6. Pure product fractions are pooled and eluted to give Compound 6 as an orange powder.

Example 6
Preparation of Compound 7
The following compound is prepared:

To a 0.25 M solution of 5'-GTP, sodium salt in water is added a 1.0 M solution of 2 equivalents of BODIPY 493/503 methyl bromide reactive dye (Molecular Probes, Eugene, Oreg.) in DMF. Saturated sodium bicarbonate solution (2 drops) is added and the resulting red solution is stirred at 40° C. for several hours. The volatiles are removed in vacuo, and the residue is purified by either column chromatography using water on SEPHADEX LH-20 or ion-exchange column chromatography on DEAE-cellulose using 0.0–50.5 M ammonium bicarbonate as eluant. In either case unreacted nucleotide elutes first, followed by the desired product. Pure product fractions are pooled and lyophilized to give Compound 7 as a red powder.

Example 7
Relative Quantum Yield Determinations for Labeled Nucleotides

An aqueous solution of a reference fluorophore, 4,4-difluoro-5,7-dimethyl-4-bora-3a,4a-diaza-s-indacene-3-propionic acid, is prepared pH 9 phosphate buffer. The concentration of this solution is matched with that of a solution of Compound 2 in the same solvent by matching the optical density (OD) at the absorption wavelength maximum, which is 504 nm for both samples. Under these conditions the solution of Compound 2 exhibits 11% of the fluorescence yield of that obtained from the reference fluorophore, when both are excited at $\lambda_{max}$ (89% quenched). This fluorescence quenching effect is diminished in a more hydrophobic solvent; in methanol the nucleotide exhibits 59% of the fluorescence yield of the reference fluorophore (41% quenched).

Under the same experimental conditions, a solution of Compound 4 exhibits 9.1% of the fluorescence of the reference fluorophore in pH 9 phosphate buffer (90.9% quenched); in methanol the nucleotide exhibits 75% of the fluorescence yield of the reference fluorophore (25% quenched).

Example 8
Fluorescent Thin Layer Chromatography Enzyme Assays

Figure 1A:
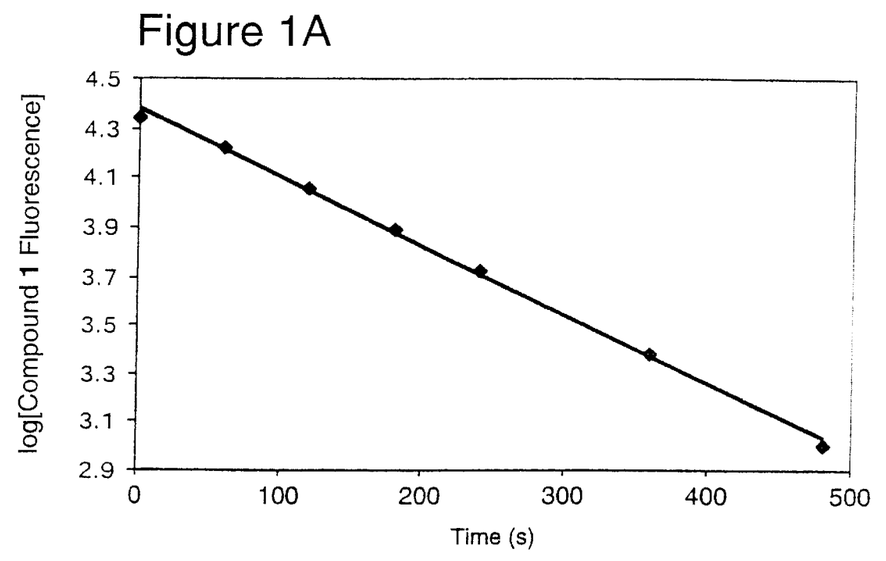
FIG. 1A) Compound 1.
Figure 1B:
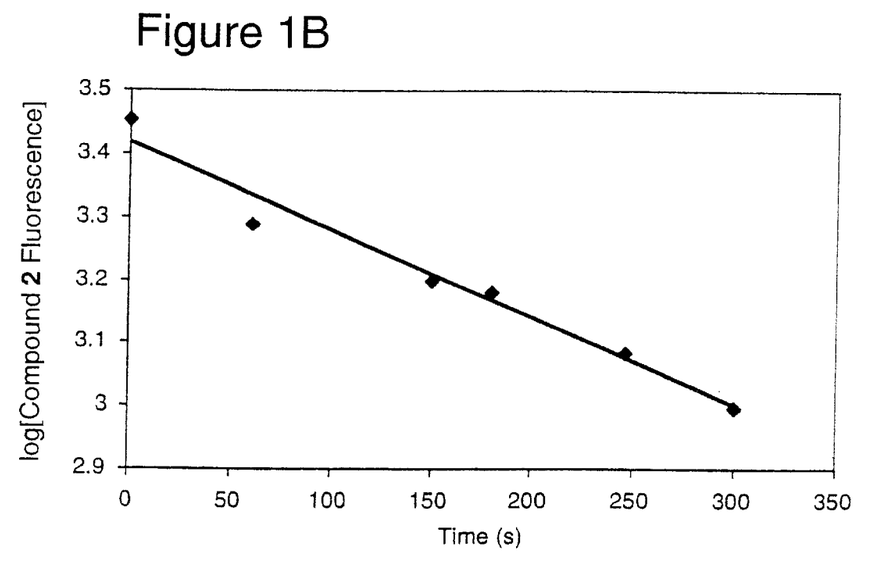
FIG. 1B) Compound 2.

Compounds 1 and 2 are incubated with purified Fhit protein at 37° C. at a substrate concentration of 1–30 μM in 20 mM Na HEPES, pH 7.0, 0.5 mM MnCl$_2$, and 0.2 mg/mL bovine serum albumin. Competitive compounds are mixed with the fluorescent substrate at eight to ten concentrations, surrounding the K$_m$ or K$_I$ values of the competitor. Reaction samples (<5 μL) are spotted on silica TLC plates at 60–120 second intervals. Plates are air-dried and developed in 2-propanol:NH$_4$OH:1,4-dioxane:H$_2$O(50:35:8:7 for Compound 1, 50:33:6:11 for Compound 2). Developed plates are imaged by epi-UV illumination and quantitated on a BioRad Fluor-S instrument (FIG. 1). For first-order decay assays, fluorescence of Compound 1 minus background fluorescence is obtained in arbitrary units. Plots of log[remaining substrate] against time yield experimental slopes, having units of s$^{-1}$, which are multiplied by −1/[enzyme] to obtain values of k$_{cat}$/K$_m$ or k$_{cat}$/K$_m$ apparent. For calculation of K$_I$ (or K$_m$) in competitive inhibition assays, k$_{cat}$/K$_m$ apparent values are plotted against [I] and values of k$_{cat}$/K$_m$ and K$_I$ (or K$_m$) are determined using the equation in Scheme 1:

$$k_{cat}/K_m(apparent) = k_{cat}/K_m - \frac{[I](k_{cat}/K_m)}{[I] + K_I} \quad \text{Scheme 1}$$

In these experiments, the value for k$_{cat}$/K$_m$ is treated as an independent variable, but is always within 15% of the experimentally determined value. For initial rate assays, the fluorescence of the diphosphate-fluorophore product is converted to pmol with a standard product curve and k$_{cat}$ and K$_m$ values are derived from Lineweaver-Burk plots (Jencks, CATALYSIS IN CHEMISTRY AND ENZYMOLOGY (1987)).

Example 10
Fluorogenic Enzyme Assays

Reactions in black 96-well plates containing Compound 2 at 1.25 to 40 μM in 60 μL of 20 mM Na HEPES, pH 7.0, 0.5 mM MnCl$_2$, and 0.2 mg/mL bovine serum albumin are initiated with the addition of 167 fmole of Fhit and incubated for 300–360 seconds at 37° C. Duplicate reactions are stopped by the addition of 60 μL 200 mM Na Citrate pH 3.0 and read with a Wallac Victor Multilabel Counter 1420 with a 485 nm excitation filter and a 535 nm emission filter. At each substrate concentration, mock reactions are created by mixing 0%, 5% and 10% volumes of acid-stopped complete hydrolysates with acid-stopped mock reactions (100%, 95%, and 90%). Fluorescent emissions are counted and plotted against pmol of diphosphate-fluorophore product produced to generate standard curves. To prove that ApppA, pyrophosphate and AMP are competitive inhibitors, these compounds are titrated into 96-well Compound 2 assays at four concentrations at each of five concentrations of Compound 2. Initial rates as a function of Compound 2 and inhibitor concentration are plotted by the method of Eadie and Hofstee (Jencks, supra).

It is to be understood that, while the foregoing invention has been described in detail by way of illustration and example, numerous modifications, substitutions, and alterations are possible without departing from the spirit and scope of the invention as described in the following claims.

What is claimed is:

1. A compound of the formula and the biologically compatible salts and esters thereof, wherein k is 1, 2, or 3;

each W is independently OH or an -X-LINK-FLUOR moiety, provided that exactly one W is an -X-LINK-FLUOR moiety;

Z and Y are independently H or OH;

BASE is a purine or pyrimidine base;

X is O, S, or NR$^9$, where R$^9$ is H, or C$_1$–C$_6$ alkyl;

LINK is a covalent linkage; and

FLUOR is a borapolyaza-s-indacene dye.

2. A compound, as claimed in claim 1, having the formula and the biologically compatible salts and esters thereof.

3. A compound, as claimed in claim 1, wherein FLUOR is a 4,4-difluoro-4-bora-3a,4a-diaza-s-indacene.

4. A compound, as claimed in claim 1, wherein FLUOR has the structure wherein FLUOR is attached to LINK at one of R$^1$–R$^7$; and for the remainder of R$^1$–R$^7$ at which LINK is not attached:

R$^7$ is N; or C—R$^8$;

R$^1$, R$^2$, R$^3$, R$^4$, R$^5$, R$^6$, and R$^8$, which may be the same or different, are hydrogen, halogen, nitro, sulfo, cyano, alkyl, perfluoroalkyl, alkoxy, alkenyl, alkynyl, cycloalkyl, arylalkyl, or acyl, wherein the alkyl portions of each contain fewer than 20 carbons; or aryl or heteroaryl; or adjacent substituents R$^1$ and R$^2$, and adjacent substituents R$^5$ and R$^6$, when taken in combination form a fused benzo ring that is optionally substituted by hydrogen, halogen, nitro, sulfo, cyano, alkyl, perfluoroalkyl, alkoxy, alkenyl, alkynyl, cycloalkyl, alkylthio, alkylamido, amino, monoalkylamino or dialkylamino wherein the alkyl portions of each contain fewer than 20 carbons; or substituted or unsubstituted aryl, heteroaryl, aryl-amido, heteroaryl-amido, aryl-oxy, heteroaryl-oxy, aryl-amino, or heteroaryl-amino; or the one or more fused benzo rings are substituted by 1–2 additional fused benzo or heteroaromatic rings.

5. A compound, as claimed in claim 1, wherein BASE is a purine base.

6. A compound, as claimed in claim 5, wherein BASE has the formula wherein W is H, $NH_2$, SH, Cl, Br, I, or $N_3$.

7. A compound, as claimed in claim 6, wherein W is H or Br.

8. A compound, as claimed in claim 1, wherein BASE is an adenine or a guanine.

9. A compound, as claimed in claim 1, wherein LINK is a covalent linkage having 1–20 nonhydrogen atoms selected from the group consisting of C, N, O, P, and S; and is composed of any combination of ether, thioether, amine, ester, carboxamide, sulfonamide, hydrazide bonds and aromatic or heteroaromatic bonds.

10. A compound, as claimed in claim 9, wherein X is S.

11. A compound, as claimed in claim 1, wherein FLUOR is a 4,4-difluoro-4-bora-3a,4a-diaza-s-indacene; BASE is a guanine; k is 3; Z is OH; Y is OH; and X is S.

12. A compound, as claimed in claim 1, wherein FLUOR has the formula or the formula or the formula 13. A method of analyzing enzyme activity in a sample, comprising:

a) adding to the sample a compound of the formula and the biologically compatible salts and esters thereof, wherein k is 1, 2, or 3;

each W is independently OH or an -X-LINK-FLUOR moiety, provided that exactly one W is an -X-LINK-FLUOR moiety;

Z and Y are independently H or OH;

BASE is a purine or pyrimidine base;

X is O, S, or $NR^9$, where $R^9$ is H, or $C_1$–$C_6$ alkyl;

LINK is a covalent linkage; and

FLUOR is a borapolyaza-s-indacene dye;

b) incubating the sample for a time sufficient for an enzyme present in said sample to cleave the compound, resulting in generation of a fluorescent hydrolysis product;

c) detecting the generation of the fluorescent hydrolysis product; and d) correlating the generation of the fluorescent hydrolysis product with the amount or activity of the enzyme.

14. A method, as claimed in claim 13, wherein the enzyme is a phosphodiesterase enzyme.

15. A method, as claimed in claim 14, where the phosphodiesterase enzyme is a nucleotide hydrolase.

16. A method, as claimed in claim 15, wherein said nucleotide hydrolase is FHIT.

17. A method, as claimed in claim 13, further comprising the step of separating the fluorescent hydrolysis product from the sample.

18. A method, as claimed in claim 17, wherein said separating step is accomplished by chromatography or electrophoresis.

19. A method, as claimed in claim 17, wherein the fluorescent hydrolysis product is not separated from the sample before the detecting step.

20. A method, as claimed in claim 19, wherein said compound is detectably less fluorescent than said fluorescent hydrolysis product.

21. A method, as claimed in claim 13, wherein BASE is a guanine.

22. A method, as claimed in claim 13, wherein a known or suspected inhibitor of the enzyme is present in the sample, and the activity of the enzyme is correlated with the presence or activity of the inhibitor.

23. A method of detecting protein binding in a sample, comprising:

a) adding to the sample a compound of the formula and the biologically compatible salts and esters thereof, wherein k is 1, 2, or 3;

each W is independently OH or an -X-LINK-FLUOR moiety, provided that exactly one W is an -X-LINK-FLUOR moiety;

Z and Y are independently H or OH;

BASE is a purine or pyrimidine base;

X is O, S, or $NR^9$, where $R^9$ is H, or $C_1$–$C_6$ alkyl;

LINK is a covalent linkage; and

FLUOR is a borapolyaza-s-indacene dye;

b) incubating the sample for a time sufficient for a protein present in said sample to bind to the compound, resulting in a detectable optical response;

c) detecting the detectable optical response; and d) correlating the detectable optical response with the binding of the compound to the protein.

24. A method, as claimed in claim 23, further comprising the step of comparing the detectable optical response to a standard.

25. A method, as claimed in claim 23, wherein the detectable optical response is a change in fluorescence intensity.

26. A method, as claimed in claim 23, wherein the detectable optical response is a change in fluorescence lifetime.

27. A method, as claimed in claim 23, wherein the detectable optical response is a change in fluorescence polarization.

28. A method, as claimed in claim 23, wherein FLUOR is a 4,4-difluoro-4-bora-3a,4a-diaza-s-indacene; BASE is a guanine; Y is OH; X is S; and the protein is a G-protein.

29. A method, as claimed in claim 23, wherein a known or suspected competitive binding moiety is present in the sample, and the binding of the compound is correlated with the presence or activity of the competitive binding moiety.

* * * * *